(12) United States Patent
Campbell et al.

(10) Patent No.: US 10,732,502 B2
(45) Date of Patent: Aug. 4, 2020

(54) CLICK-CHEMISTRY COMPATIBLE STRUCTURES, CLICK-CHEMISTRY FUNCTIONALIZED STRUCTURES, AND MATERIALS AND METHODS FOR MAKING THE SAME

(71) Applicant: Lawrence Livermore National Security, LLC, Livermore, CA (US)

(72) Inventors: Patrick Campbell, Oakland, CA (US); Eric Duoss, Dublin, CA (US); James Oakdale, Castro Valley, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 202 days.

(21) Appl. No.: 15/253,654

(22) Filed: Aug. 31, 2016

(65) Prior Publication Data

US 2018/0059541 A1 Mar. 1, 2018

(51) Int. Cl.
*G03F 7/00* (2006.01)
*C09D 5/08* (2006.01)
(Continued)

(52) U.S. Cl.
CPC .......... *G03F 7/0037* (2013.01); *A01N 25/10* (2013.01); *A61K 47/58* (2017.08); *B29C 64/129* (2017.08);
(Continued)

(58) Field of Classification Search
CPC .......... G03F 7/004; G03F 7/075; G03F 7/008; G03F 7/025; G03F 7/027; G03F 7/20;
(Continued)

(56) References Cited

U.S. PATENT DOCUMENTS

| 2,982,941 A | 5/1961 | Chun |
| 3,254,115 A | 5/1966 | Cohen et al. |

(Continued)

FOREIGN PATENT DOCUMENTS

| CN | 103408746 A | 11/2013 |
| CN | 104086749 A | 10/2014 |

(Continued)

OTHER PUBLICATIONS

Lutz et al, "Efficient construction of therapeutics, bioconjugates, biomaterials and bioactive surfaces using azide-alkyne click" chemistry, Advanced Drug Delivery Reviews, 60 (2008), 958-970.*

(Continued)

*Primary Examiner* — Amanda C. Walke
(74) *Attorney, Agent, or Firm* — Zilka-Kotab, P.C.

(57) ABSTRACT

According to various embodiments, systems, methods, and computer program products for click-chemistry compatible structures, additive manufacturing resins for forming the same, and method of formation of such structures and resins, as well as techniques for functionalizing click-chemistry compatible structures are disclosed. The inventive structures generally include a plurality of photo polymerized molecules structurally arranged according to a three-dimensional pattern, while surfaces of the structure are functionalized with one or more click-chemistry compatible molecules each having one or more click-chemistry compatible functional groups. The structures may be formed from single- or dual-component resins, each having unique synthetic pathways. The resulting structures may be functionalized for utility in a wide range of applications by leveraging click chemistry to further functionalize the structure with organic additives also compatible with click-chemistry reaction schemes.

20 Claims, 8 Drawing Sheets

(51) Int. Cl.

| | |
|---|---|
| C09D 5/16 | (2006.01) |
| A01N 25/10 | (2006.01) |
| G03F 7/027 | (2006.01) |
| G03F 7/025 | (2006.01) |
| G03F 7/008 | (2006.01) |
| B33Y 10/00 | (2015.01) |
| B33Y 70/00 | (2020.01) |
| B33Y 80/00 | (2015.01) |
| G03F 7/038 | (2006.01) |
| A61K 47/58 | (2017.01) |
| C09D 5/14 | (2006.01) |
| B29C 64/129 | (2017.01) |
| C08F 2/60 | (2006.01) |
| C08F 2/50 | (2006.01) |

(52) U.S. Cl.
CPC .............. *B33Y 10/00* (2014.12); *B33Y 70/00* (2014.12); *B33Y 80/00* (2014.12); *C08F 2/50* (2013.01); *C08F 2/60* (2013.01); *C09D 5/08* (2013.01); *C09D 5/14* (2013.01); *C09D 5/1662* (2013.01); *G03F 7/008* (2013.01); *G03F 7/0085* (2013.01); *G03F 7/025* (2013.01); *G03F 7/027* (2013.01); *G03F 7/038* (2013.01)

(58) Field of Classification Search
CPC .......... C09D 5/08; C09D 5/16; C09D 133/08; C09D 141/00; C09D 163/00
USPC .......................................................... 430/18
See application file for complete search history.

(56) References Cited

U.S. PATENT DOCUMENTS

| | | | |
|---|---|---|---|
| 4,891,438 | A | 1/1990 | Ahad |
| 5,756,261 | A | 5/1998 | Takehana et al. |
| 2007/0219218 | A1 | 9/2007 | Yu et al. |
| 2008/0200631 | A1 | 8/2008 | Haring et al. |
| 2009/0098467 | A1 | 4/2009 | Lowe et al. |
| 2013/0137252 | A1 | 5/2013 | Iida et al. |
| 2018/0059540 | A1 | 3/2018 | Campbell et al. |
| 2018/0329296 | A1 | 11/2018 | Campbell et al. |

FOREIGN PATENT DOCUMENTS

| | | |
|---|---|---|
| EP | 119017 A2 | 9/1984 |
| WO | 2015084753 A1 | 6/2015 |

OTHER PUBLICATIONS

Babensee et al, "On-Surface Azide-Alkyne Cycloaddition on Cu(!!!): Does It "Click" in Ultrahigh Vacuum?", Journal of the American Chemical Society (2013), 135, 2136-2139.*
Lowe, "Thiol-ene "click" reactions and recent applications in polymer andmaterials synthesis: a first update", Polymer Chemistry, 5, 4820-4870 (2014).*
Durmaz et al., "Surface Modification of UV-Cure Epoxy Resins by Click Chemistry", Journal of Polymer Science Part A: Polymer Chemistry, vol. 48, 2862-2868 (2010).*
Restriction Requirement from U.S. Appl. No. 15/253,640, dated Nov. 15, 2017.
Campbell et al., U.S. Appl. No. 15/253,640, filed Aug. 31, 2016.
Kantheti et al., "The impact of 1,2,3-triazoles in the design of functional coatings," RSC Advances, vol. 5, No. 5, 2015, pp. 3687-3708.
Bentiss et al., "Electrochemical Study of Substituted Triazoles Adsorption on Mild Steel," Industrial & Engineering Chemistry Research, vol. 39, No. 10, 2000, pp. 3732-3736.
Ho et al., "Quorum sensing inhibitory activities of surface immobilized antibacterial dihydropyrrolones via click chemistry," Biomaterials, vol. 35, No. 7, 2014, pp. 2336-2345.
Wang et al., "The promotion of antimicrobial activity on silicon substrates using a 'click' immobilized short peptide," Chemical Communications, vol. 50, No. 8, 2014, pp. 975-977.
Yang et al., "Barnacle Cement as Surface Anchor for 'Clicking' of Antifouling and Antimicrobial Polymer Brushes on Stainless Steel," Biomacromolecules, vol. 14, No. 6, 2013, pp. 2041-2051.
Sun et al., "Triazole-forming waterborne polyurethane composites fabricated with silane coupling agent functionalized nano-silica," Journal of Colloid and Interface Science, vol. 361, No. 2, 2011, pp. 483-490.
Hein et al., "Copper-catalyzed azide-alkyne cycloaddition (CuAAC) and beyond: new reactivity of copper(i) acetylides," Chemical Society Reviews, vol. 39, No. 4, 2010, pp. 1302-1315.
Zheng et al., "Design and optimization of a light-emitting diode projection micro-stereolithography three-dimensional manufacturing system," Review of Scientific Instruments, vol. 83, No. 12, 2012, pp. 1-7.
Quick et al., "Rapid Thiol-Yne-Mediated Fabrication and Dual Postfunctionalization of Micro-Resolved 3D Mesostructures," Advanced Functional Materials, vol. 25, No. 24, 2015, pp. 3735-3744.
Becer et al., "Click Chemistry beyond Metal-Catalyzed Cycloaddition," Angew. Chem. Int. Ed., vol. 48, 2009, pp. 4900-4908.
Wang et al., "Metal-catalyzed azide-alkyne "click" reactions: Mechanistic overview and recent trends," Coordination Chemistry Reviews, vol. 316, Jun. 2016, pp. 1-20.
Non-Final Office Action from U.S. Appl. No. 15/253,640, dated Mar. 21, 2018.
Zhang et al., "Multiblock sequence-controlled glycopolymers via Cu(0)-LRP following efficiency thiol-halogen, thiol-epoxy and CuAAC reactions," Polymer Chemistry, vol. 5, 2014, pp. 3876-3883 & Supporting Information, 19 pages.
Murtezi et al., "Synthesis of clickable hydrogels and linear polymers by type II photoinitiation," Polymer International, vol. 64, 2014, pp. 588-594.
Krieg et al., "Tailor Made Side-Chain Functionalized Macromolecules by a Combination of Controlled Radical Polymerization and Click Chemistry," Macromolecular Symposia, vol. 275-276, 2009, pp. 73-81.
Li et al., "Low temperature cross-linked, high performance polymer gate dielectrics for solution-processed organic field-effect transistors", Polymer Chemistry, vol. 6, 2015, pp. 5884-5890.
Green et al., "Protection for the Alkyne-CH", Protective Groups in Organic Synthesis, Third Edition, Chapter 8, 1999, pp. 654-659.
Slavin et al., "Synthesis of glycopolymers via click reactions," European Polymer Journal, vol. 47, 2011, pp. 435-446.
Grogna et al., "Stealth macromolecular platforms for the design of MRI blood pool contrast agents," Polymer Chemistry, vol. 2, 2011, pp. 2316-2327.
Campbell et al., U.S. Appl. No. 16/045,621, filed Jul. 25, 2018.
Non-Final Office Action from U.S. Appl. No. 15/253,640, dated Aug. 3, 2018.
Durmaz et al., "Surface Modification of UV-Cured Epoxy Resins by Click Chemistry," Journal of Polymer Science, Part A, vol. 48, 2010, pp. 2862-2868.
Doran et al., "Tandem Photoiniduced Cationic Polymerizatrion and CuAAC for Macromolecular Synthesis," Macromolecules, vol. 48, 2015, pp. 7446-7452.
Hilf et al., "Propargyl-Functional Aliphatic Polycarbonate Obtained form Carbon Dioxide and Glycidyl Propargyl Ether," Macromolecular Rapid Communications, vol. 34, 2013, pp. 1395-1400.
Final Office Action from U.S. Appl. No. 15/253,640, dated Feb. 4, 2019.
Examiner's Answer to Appeal Brief from U.S. Appl. No. 15/253,640, dated Sep. 13, 2019.
Lowe, A., "Thiol-ene "click" reactions and recent applications in polymer and materials synthesis: a first update," Polymer Chemistry, 2014, pp. 4820-4870.
Mizuno et al., "Ring opening reaction of epoxides with diphenyl phosphorazidate," Tetrahedron Letters, vol. 40, 1999, pp. 7105-7108.

(56) References Cited

OTHER PUBLICATIONS

Yu et al., "Thiol-ene Photocrosslinked Hybrid Vesicles Based on the co-assembly of POSS and Poly(ether amine) (PEA)," Supporting Information, The Royal Society of Chemistry, Electronic Supplementary Material (ESI) for Chemical Communications, 2011, pp. 1-10.

* cited by examiner

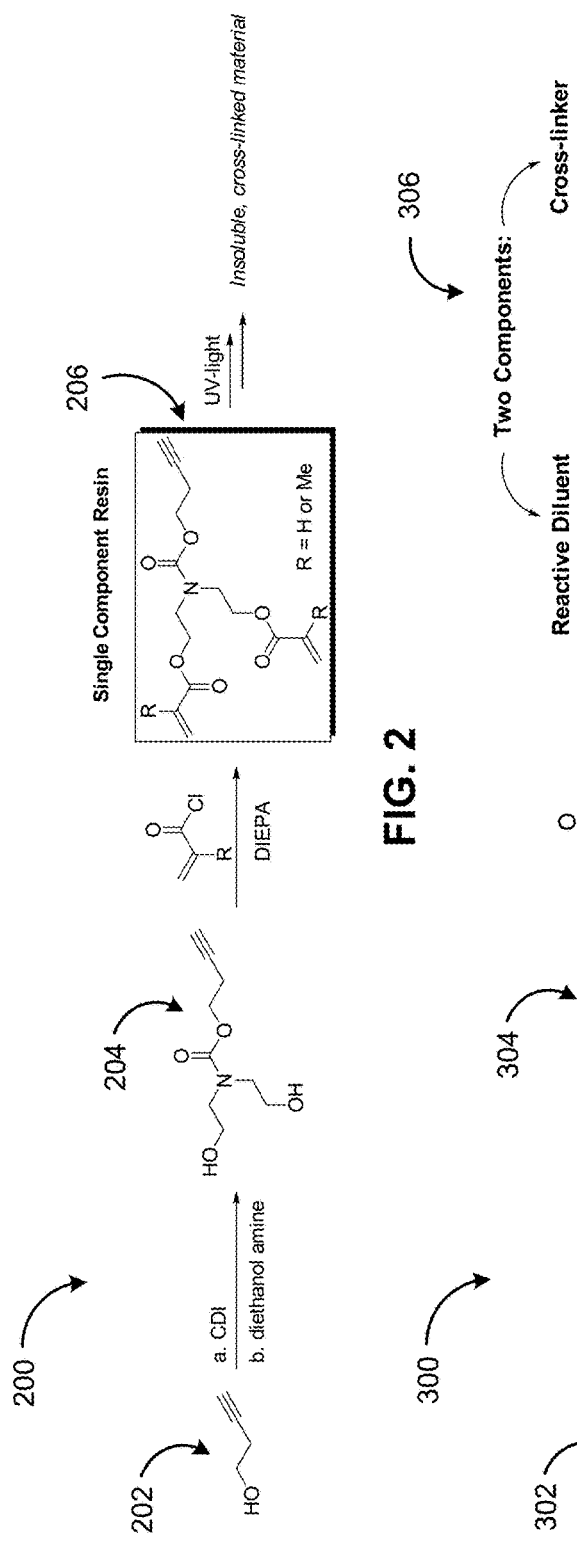
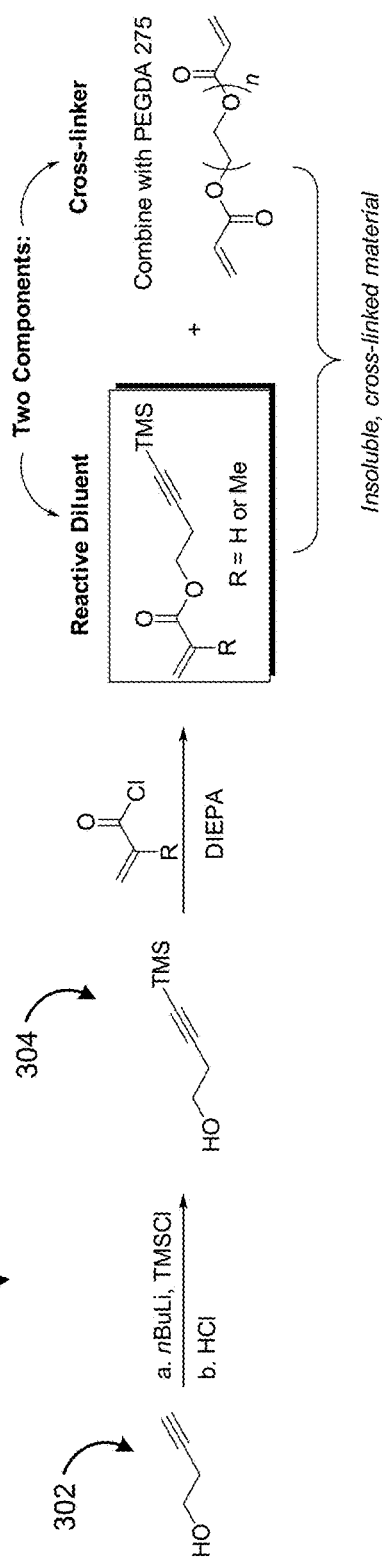
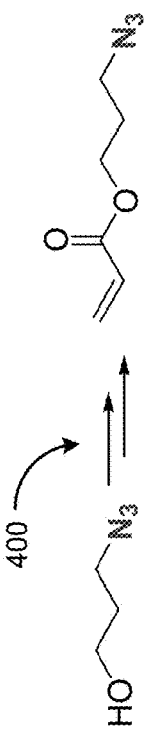
FIG. 2
FIG. 3
FIG. 4

PG = Trialkylsilylacetylenes
 1. SiMe$_3$ (trimethylsilyl; TMS) - deprotection with flouride, silver nitrate, alkali conidtions
 2. SiEt$_3$ (triethylsilyl; TES) - deprotection with flouride, silver nitrate, alkali conidtions
 3. Si(Me)$_2$tBu (t-butyldimethylsilyl; TBS) - fluoride
 4. Si(iPr)$_3$ (triisopropyl; TIPS) - fluoride, better alkali stability PG = 2-(2-Hydroxypropyl)alkyne - deprotection with refluxing NaOH.

FIG. 7A

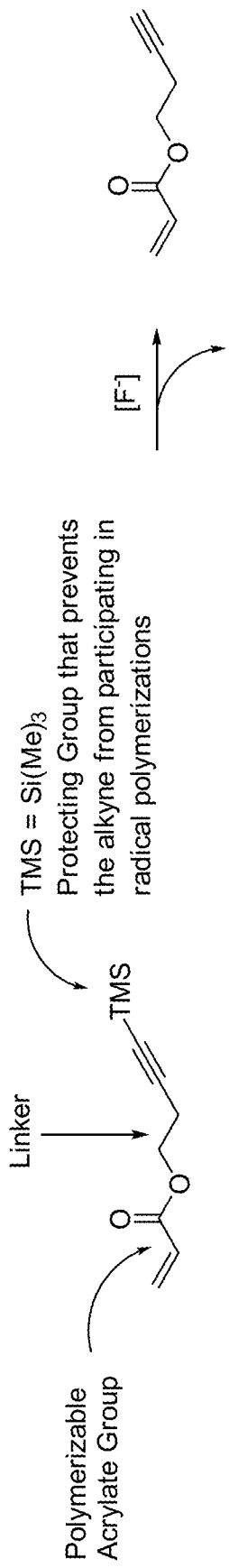

Linker
TMS
TMS = Si(Me)$_3$
Protecting Group that prevents the alkyne from participating in radical polymerizations Polymerizable Acrylate Group

[F$^-$]
TMS-F

FIG. 7B

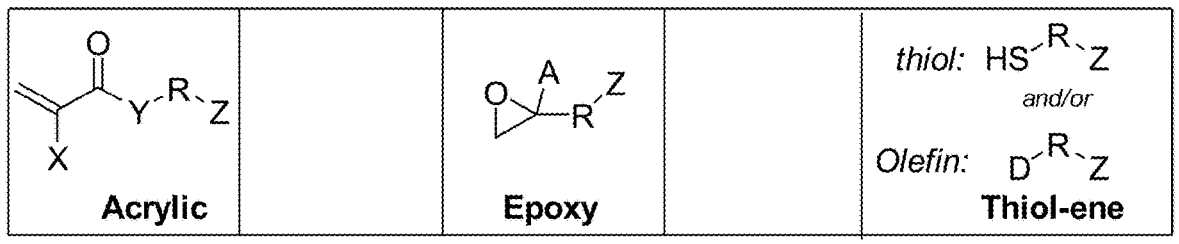

| Acrylic | | Epoxy | | Thiol-ene |

X =     -H or -CH$_3$, *could also include* -C$_n$H$_{2n+1}$

Y =     -O- (acrylate) or -NH- (acrylamide),
*could also include* -CH$_2$-, or -N(C$_n$H$_{2n+1}$)-

Z = Organic Alkyne: 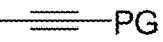

= Organic Azide: 

A =     -H, *could also include* -(C$_n$H$_{2n+1}$)

D = Olefin, examples inlude; 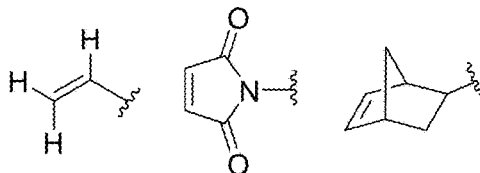

R = *Linker:*   aliphatic; -(CH$_2$)$_n$-
            polyethylene glycol; -(C$_2$H$_4$O)$_n$-

Aromatic;      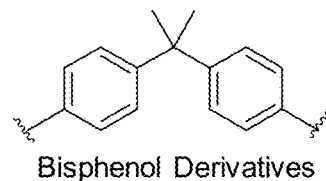

Phenyl (*n* = 0), Benzyl (*n* = 1)     Bisphenol Derivatives

Dimethylsiloxane;   -(SiMe$_2$O)$_n$-

*Linker may also contain any of the following function groups*
    Ester; -RC(O)OR-
    Amide; -RC(O)NR$_n$- where n = 1 or 2 and R = H or as defined above
    Amine; -RNR$_2$- where n = 1 or 2 and R = H or as defined above
    Ether; -ROR-
    Urea; -R$_n$NC(O)NR$_n$- where n = 1 or 2 and R = H or as defined above
    Carbamate; - ROC(O)NR$_2$- where n = 1 or 2 and R = H or as defined above
    Carbonate; -ROC(O)OR-
    Sulfone; -RSO$_2$R-

FIG. 16

CLICK-CHEMISTRY COMPATIBLE STRUCTURES, CLICK-CHEMISTRY FUNCTIONALIZED STRUCTURES, AND MATERIALS AND METHODS FOR MAKING THE SAME

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The presently disclosed inventive concepts relate to additive manufacturing techniques and compositions, and particularly to compositions suitable for use in additive manufacturing to fabricate structures that are compatible with click-chemistry, as well as structures that have been functionalized via click chemistry.

BACKGROUND

In the field of additive manufacturing, many techniques exist to create structures with precise control over the features of the structure. Recently, techniques based on photo-activation of precursor components, such a projection microstereolithography (PµSL) have received significant attention. To date, such techniques have been demonstrated and proven effective for making structures that consist of crosslinked polymers in nearly any shape or configuration.

However, the structures created via these photo-activation-based additive manufacturing techniques consist of the crosslinked polymers, i.e. inert plastic. While creating such structures consisting of crosslinked polymers is itself advantageous from a manufacturing standpoint, this does not provide any chemically- and/or biologically-relevant applicability to the resulting structures.

Accordingly, it would be highly beneficial to provide techniques and suitable materials that are capable of generating structures with the precise control afforded by photo-activation-based additive manufacturing, while also enabling the resulting structure to have further functionality that is chemically- and/or biologically relevant to a variety of industrial, pharmaceutical, etc. applications.

SUMMARY

In one embodiment, a click-chemistry compatible structure includes: a plurality of photo polymerized molecules structurally arranged according to a three-dimensional pattern. Surfaces of the three-dimensional structure are functionalized with one or more click-chemistry compatible functional groups.

In another embodiment, a method of forming a click-chemistry compatible structure includes: exposing, according to a three-dimensional pattern, portions of an additive manufacturing resin to a wavelength of light configured to cause a photo polymerizable compound in the additive manufacturing resin to polymerize into a solid layer of the structure. The additive manufacturing resin comprises at least one compound having a click-chemistry compatible functional group.

In yet another embodiment, a method of functionalizing a click-chemistry compatible structure includes: reacting the click-chemistry compatible structure with an organic additive. The structure has one or more click-chemistry compatible molecules functionalized on surfaces thereof; while the organic additive includes one or more click-chemistry compatible functional groups other than click-chemistry compatible functional groups of the click-chemistry compatible molecules functionalized on the surfaces of the structure. The click-chemistry compatible molecules functionalized on the surfaces of the structure are structurally configured to react with the one or more click-chemistry compatible functional groups of the organic additive and thereby attach the organic additive to the structure via the click-chemistry compatible molecules functionalized on the surfaces of the structure.

In still yet another embodiment, an additive manufacturing resin suitable for fabricating a click-chemistry compatible structure includes a click-chemistry compatible oligomer. The click-chemistry compatible oligomer includes one or more photo polymerizable moieties.

In further embodiments, a method of forming an additive manufacturing resin suitable for fabricating a click-chemistry compatible structure includes: reacting a compound comprising a terminal alkyne group or a terminal azide group to form a photo polymerizable oligomer precursor; and reacting the photo polymerizable oligomer precursor with a compound comprising a photo polymerizable group to form the additive manufacturing resin. The precursor includes the terminal alkyne group or the terminal azide group.

Other aspects and embodiments of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, reference should be made to the following detailed description read in conjunction with the accompanying drawings.

FIG. 2 is a simplified reaction scheme for forming a single-component resin for additively manufacturing click-chemistry compatible structures, according to another embodiment.

FIG. 3 is a simplified reaction scheme for forming a dual-component resin for additively manufacturing click-chemistry compatible structures, according to another embodiment.

FIG. 4 is a simplified reaction scheme for forming a resin for additively manufacturing click-chemistry compatible structures, according to another embodiment.

FIG. 7A depicts simplified structures comprising a terminal alkyne functionalized with a protecting group, according to various embodiments.

FIG. 7B depicts simplified structures comprising a photo polymerizable compound featuring a terminal alkyne functionalized with a protecting group (left) and a reaction scheme for deprotecting the terminal alkyne to form a photo polymerizable, click-chemistry compatible molecule, according to one embodiment.

FIG. 16 depicts exemplary simplified structures suitable for use as precursor materials in photo-activation-based additive manufacturing, according to various illustrative embodiments.

DETAILED DESCRIPTION

Figure 1:
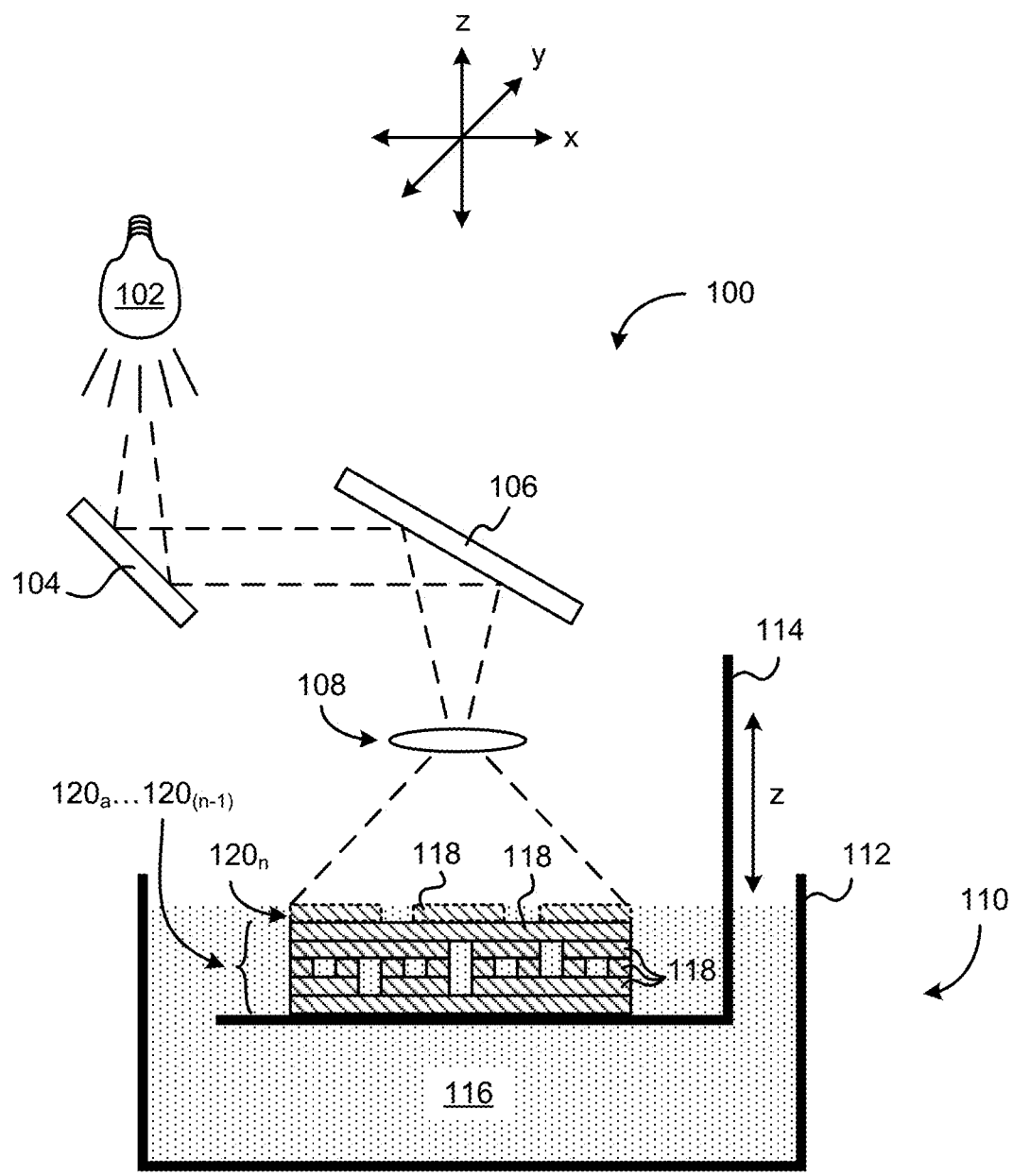
FIG. 1 is a simplified schematic of a projection microstereolithography (PµSL) apparatus, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

As also used herein, the term "about" when combined with a value refers to plus and minus 10% of the reference value. For example, a length of about 1 μm refers to a length of 1 μm±0.1 μm.

It must also be noted that, as used in the specification and the appended claims, the singular forms "a," "an" and "the" include plural referents unless otherwise specified.

As utilized herein, it should be understood that "click-chemistry compatible" structures, functional groups, monomers, oligomers, etc., refer to compounds, materials, etc. that are structurally characterized by including one or more chemical moieties suitable for participation in a click-chemistry reaction. In embodiments where copper-catalyzed azide-alkyne cycloaddition (CuAAC) is the click-chemistry employed for functionalizing materials as disclosed herein, the "click-chemistry compatible" compounds include a terminal alkyne and/or terminal azide functional group.

The exemplary and preferred click-chemistry reaction described herein is CuAAC, although skilled artisans will appreciate that other click-chemistry compatible reactions that would be appreciated as equivalent to CuAAC upon reading these descriptions may be employed without departing from the scope of the inventive concepts described herein. For instance, in various embodiments click-chemistry compatible reactions may include CuAAC, strain-promoted azide-alkyne cycloaddition (SPAAC), strain-promoted alkyne-nitrone cycloaddition (SPANC), strained alkene reactions such as alkene-azide cycloaddition, etc. Click-chemistry compatible reactions may also be considered to include alkene-tetrazine inverse-demand Diers-Alder reactions, alkene-tetrazole photoclick reactions, Michael additions of thiols, nucleophilic substitution of thiols with amines, and certain Diels-Alder reactions, etc. such as disclosed by Becer, et al. "Click chemistry beyond metal-catalyzed cycloaddition."*Angew. Chem. Int. Ed.* 2009, 48: p. 4900-4908, and equivalents thereof as would be understood by a person having ordinary skill in the art upon reading the present disclosures. Accordingly, click-chemistry compatible groups, compounds, etc. should be understood to include one or more suitable chemical moieties conveying capability to participate in any combination of the foregoing exemplary click chemistries, in various embodiments.

As described herein, "photo polymerizable" compounds, groups, etc. are structurally characterized by including one or more chemical moieties suitable for causing polymerization of the such compounds, groups, etc. under suitable environmental conditions including exposure of the photo polymerizable compound and/or an intermediate reagent (such as a photoactivator, photoinitiator, etc. as described herein and would be appreciated by skilled artisans upon reading the present disclosure). Preferred embodiments of such photo polymerizable compounds according to the presently described inventive concepts, and particularly those embodiments that employ projection microstereolithography, include: acrylates, epoxides, and thiol-enes. Of course, skilled artisans will appreciate that other photo polymerizable groups, compounds, etc. that would be appreciated as equivalent to acrylates, epoxides, and thiol-enes may be employed without departing from the scope of the present disclosures.

The following description discloses several preferred embodiments of click-chemistry compatible and/or functionalized structures, as well as related compositions, systems and methods of making the same.

In one general embodiment, a click-chemistry compatible structure includes: a plurality of photo polymerized molecules structurally arranged according to a three-dimensional pattern. Surfaces of the three-dimensional structure are functionalized with one or more click-chemistry compatible functional groups.

In another general embodiment, a method of forming a click-chemistry compatible structure includes: exposing, according to a three-dimensional pattern, portions of an additive manufacturing resin to a wavelength of light configured to cause a photo polymerizable compound in the additive manufacturing resin to polymerize into a solid layer of the structure. The additive manufacturing resin comprises at least one compound having a click-chemistry compatible functional group.

In yet another general embodiment, a method of functionalizing a click-chemistry compatible structure includes: reacting the click-chemistry compatible structure with an organic additive. The structure has one or more click-chemistry compatible molecules functionalized on surfaces thereof; while the organic additive includes one or more click-chemistry compatible functional groups other than click-chemistry compatible functional groups of the click-chemistry compatible molecules functionalized on the surfaces of the structure. The click-chemistry compatible molecules functionalized on the surfaces of the structure are structurally configured to react with the one or more click-chemistry compatible functional groups of the organic additive and thereby attach the organic additive to the structure via the click-chemistry compatible molecules functionalized on the surfaces of the structure.

In still yet another general embodiment, an additive manufacturing resin suitable for fabricating a click-chemistry compatible structure includes a click-chemistry compatible oligomer. The click-chemistry compatible oligomer includes one or more photo polymerizable moieties.

In further general embodiments, a method of forming an additive manufacturing resin suitable for fabricating a click-chemistry compatible structure includes: reacting a compound comprising a terminal alkyne group or a terminal azide group to form a photo polymerizable oligomer precursor; and reacting the photo polymerizable oligomer precursor with a compound comprising a photo polymerizable group to form the additive manufacturing resin. The precursor includes the terminal alkyne group or the terminal azide group.

Turning now to FIG. 1, a simplified schematic of an exemplary apparatus 100 for performing photocatalytic additive manufacturing, such as PµSL, is shown according to one embodiment. The apparatus 100 generally includes a synthesis portion 110 comprising a reservoir 112 and a stage 114. The reservoir 112 may comprise any suitable materials and/or configuration that would be understood by a person having ordinary skill in the art, and should be characterized by dimensions suitable to allow the stage 114 to be contained within an inner volume of the reservoir 112. The stage 114 similarly may comprise any suitable materials and/or configuration, and preferably includes a flat lower portion upon which a product may be formed via additive manufacturing. In particularly preferred approaches, the stage 114 is configured to change position within the reservoir 112 along at least a z-axis, as shown in FIG. 1. More preferably, the stage 114 may also be configured to change position within the reservoir 112 along an x and/or y axis. Alternatively, another mechanism may move the reservoir 112 along x, y and/or z axes while the stage 114 remains stationary.

The apparatus 100 further comprises an optics portion, which includes a light source 102, a digital mask 104, a mirror 106 (optional) and a projection lens 108. Each component of the optics portion is arranged to form a beam path from the light source 102 to the reservoir 112. Preferably, the light source is monochromatic, and emits a wavelength of light tuned to the photoinitiator band of the precursor 116, e.g. a photopolymer resin.

The digital mask 104 may include any suitable mask that would be understood by a person having ordinary skill in the art upon reading the present descriptions, and may in some approaches comprise an array of micro mirrors configured to selectively reflect light (dashed lines) from the light source 102 toward the mirror 106 and/or projection lens 108, or away from the mirror 106 and/or projection lens 108. In other embodiments, the digital mask 104 may include a liquid crystal on silicon (LCoS) device.

The selectivity of the reflection may be defined based on a computer-generated digital pattern corresponding to a layer $120a \ldots 120_n$ of a structure to be created using the apparatus 100. Accordingly, the apparatus 100 may be communicatively coupled to a computer or other suitable device and receive therefrom instructions regarding a particular pattern or series of patterns to utilize for selectively directing light from the light source 102 to the reservoir 112 as part of an additive manufacturing process.

Accordingly, in operation, apparatus 100 facilitates the manufacture of custom-designed structures with extreme precision, e.g. characterized by a feature size on the scale of $10^{-2}$-$10^3$ microns, in some embodiments. In various embodiments, features may be characterized by a feature size on the scale of 10 nm to several hundred (e.g. 300-500) nm, a feature size on the scale of several hundred nm to several hundred microns, a feature size on the scale of several hundred nm to several mm, etc., e.g. including embodiments in which the feature size may be in a range determined based on the type of formation process employed to fabricate the structures and as would be understood by a person having ordinary skill in the art upon reviewing the present disclosures.

As described herein, features should be understood to include any suitable component, portion, etc. of a three-dimensional structure, as would be understood by a person having ordinary skill in the art upon reading the present descriptions. For instance, in various embodiments, features may include protrusions, depressions, voids, lattices, channels, pockets, pillars, points, overhangs, cantilevers, positive features at various angles, etc. as skilled artisans will appreciate upon reviewing the instant disclosure. Generally, and due to the high level of precision afforded by PµSL, any of the foregoing features may be formed at nearly any angle.

To accomplish this result, a precursor 116 is placed in the reservoir 112, and the stage 114 is positioned within the reservoir 112 in such a manner that the lower portion of the stage 114 is submerged in the precursor 116 to a predetermined depth corresponding to a thickness of a layer $120a \ldots 120n$ of the structure to be fabricated.

The precursor 116 may include any suitable material, and preferably includes one or more photo-curable resins. In various approaches, the precursor 116 is preferably a liquid, optionally a viscous liquid, and may include one or more photopolymers, e.g. a combination of photoinitiator and oligomers, such as hexane diol diacrylate (HDDA), polyethylene glycol diacrylate (PEGDA), pentaerythritol triacrylate (PETA) ethylene glycol dimethacrylate (EGDMA), epoxides, silicones, thiol-enes, and/or other suitable photopolymers for forming a solid structure via PµSL that would be understood by a person having ordinary skill in the art upon reading the present disclosure. Precursor 116 may be in the form of a solution, a mixture, etc. and may optionally include photoactive reduction inhibitor(s), photo reductant(s) and/or photoabsorber(s). In preferred approaches at least two of the foregoing optional compositions are included, and in particularly preferred embodiments at least the photoabsorber, which advantageously enhances feature resolution by decreasing the resin's sensitivity to light, is present.

The photo-curable resin(s) are characterized by forming solids, e.g. via crosslinking polymers in the precursor 116, in response to exposure of the precursor 116 to light (dashed lines) from the light source 102. Accordingly, it is possible to define a precise three-dimensional structure via a series of patterns to be applied via the digital mask 104 and selectively expose a predetermined thickness/depth of the precursor 116 to the light from light source 102 and form, layer-by-layer, regions 118 of solid material from the precursor 116.

As shown in FIG. 1, the structure formed using the apparatus 100 thus includes a plurality of layers 120a . . . 120n each formed according to a single exposure from the light source 102 and according to a pattern defined by the digital mask 104. In between formation of each layer 120a . . . 120n, the stage 114 is moved within the reservoir (and/or the reservoir 112 is moved relative to the stage 114) to facilitate formation of a subsequent layer on the previously formed layer. According to FIG. 1, the structure is characterized by a plurality of layers 120a . . . 120$_{(n-1)}$, and the apparatus 100 is in the process of forming a final layer 120n on layer 120$_{(n-1)}$ by exposing precursor 116 above layer 120$_{(n-1)}$ to light from the light source 102. In response to the exposure, in the regions 118 to which the precursor 116 is exposed the photopolymer initiates a crosslinking process and solidifies in the corresponding regions 118 (shown by dashed line rectangles in layer 120n of FIG. 1).

In the foregoing manner, extremely precise control over structural and positional arrangement of the resulting component is enabled. While the structure shown in FIG. 1 has a substantially rectangular, simple profile and arrangement of component portions, more complex structures such as shown in FIGS. 2A-2B are equally feasible, in various approaches.

The foregoing descriptions of an apparatus 100 as shown in FIG. 1 and a corresponding fabrication process should be understood as exemplary, nonlimiting illustrations of a suitable apparatus 100 and fabrication process suitable for use in the context of the presently disclosed inventive concepts. It will be appreciated by a person having ordinary skill in the art upon reading the present descriptions that other apparatuses and/or fabrication processes, particularly additive manufacturing and three-dimensional printing processes such as stereolithography, deposition modeling, continuous liquid interface production and binder printing may be employed without departing from the scope of the instant descriptions.

However, in preferred approaches an apparatus 100 as shown in FIG. 1 and PμSL manufacturing process are implemented to form structures having click-chemistry compatible groups, e.g. terminal azides and/or alkynes, functionalized on surfaces thereof. The surfaces may include outer surfaces, as well as surfaces of pores that may optionally be present throughout portions or an entirety of the structure.

Accordingly, it should be appreciated that the presently disclosed inventive concepts represent a novel technique for generating selectively functionalized structures via additive manufacturing and/or three-dimensional printing processes. The novel techniques result in novel structures with click-chemistry compatible functional groups on surfaces thereof, which advantageously allows for a variety of further surface functionalization using a variety of organic additives also characterized by having functional group(s) compatible with click-chemistry such as copper-catalyzed azide alkyne cycloaddition (CuAAC) reaction schemes. Other suitable chemistries may be employed without departing from the scope of the present disclosures, as described in further detail herein, such as the exemplary chemistries set forth herein.

As discussed above with reference to FIG. 1 photo-activated additive manufacturing techniques such as projection microstereolithography may advantageously be leveraged to form chemically- and/or biologically-relevant structures that are compatible with click-chemistry and/or functionalized via click-chemistry. Such functionalization preferably provides additional functional capabilities to the structures, via surface modification configured to add a variety of organic additives advantageous or suitable to a particular application, such as the exemplary applications and uses described in further detail below.

In order to form structures that are click-chemistry compatible and convey the advantageous additional functionality discussed herein, it is necessary to utilize precursor materials that are unique from the conventional precursor materials employed to-date for photo-activated additive manufacturing. The presently disclosed inventive concepts therefore include embodiments comprising unique synthetic pathways for generating precursor materials that are suitable for photo-activated additive manufacturing of structures that are click-chemistry compatible.

Figure 13:
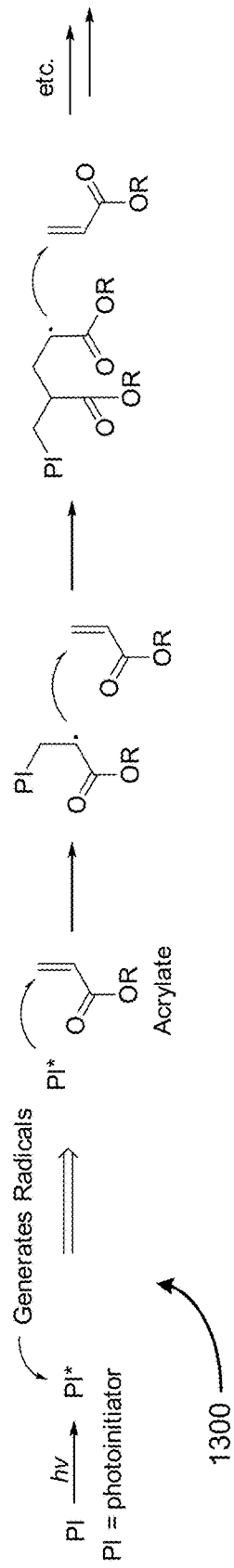
FIG. 13 depicts a simplified reaction scheme for photo-activation-based additive manufacturing using precursor materials comprising acrylate functional groups, in one approach.
Figure 14:
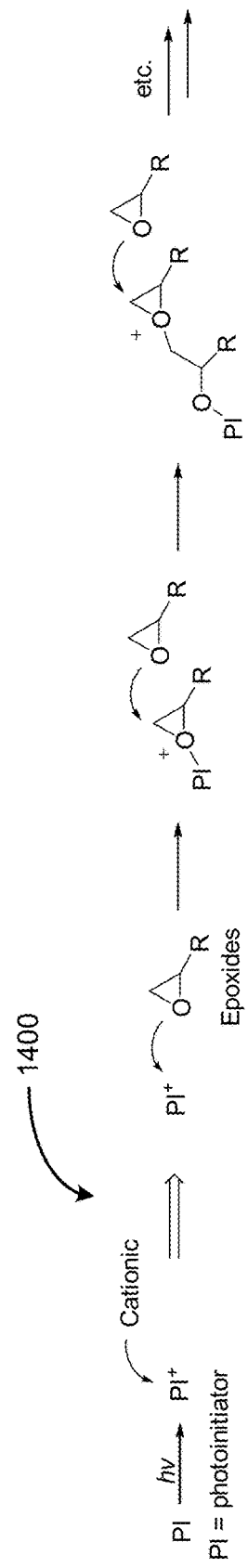
FIG. 14 depicts a simplified reaction scheme for photo-activation-based additive manufacturing using precursor materials comprising epoxide functional groups, in one approach.
Figure 15:
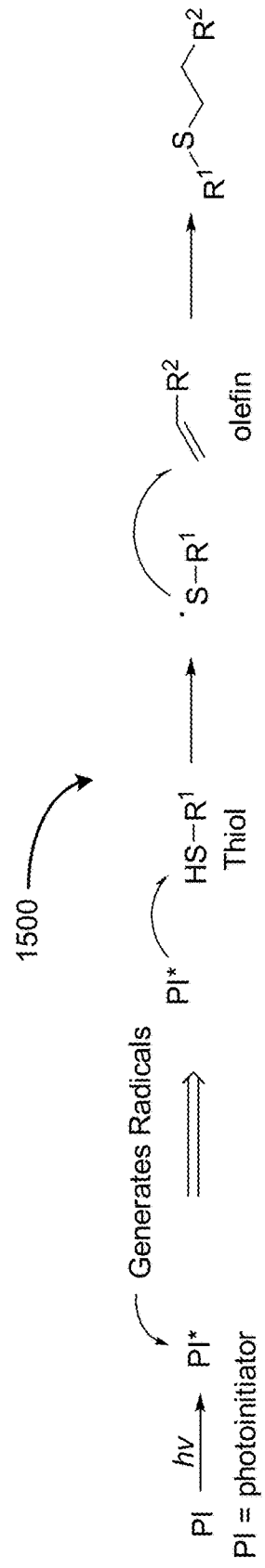
FIG. 15 depicts a simplified reaction scheme for photo-activation-based additive manufacturing using precursor materials comprising thiol-ene functional groups, in one approach.

For instance, in one approach, a simplified reaction scheme 200 for forming a single-component resin is shown in FIG. 2. The single-component resin is suitable for use in for additively manufacturing click-chemistry compatible structures. As discussed herein, the term "single-component" refers to the existence of a single component that participates in the photo-activated additive manufacturing reaction (e.g. as shown in FIGS. 13-15, and described in further detail below). Those having ordinary skill in the art will appreciate, upon reading the instant disclosures, that the resin according to various embodiments may include other materials, such as photoactivators, photoabsorbers, photoinitators, etc. In further embodiments, single-component resins may include multiple different types of functional group(s) suitable for photo-activated additive manufacturing, such as acrylates (shown in FIG. 2), epoxides, thiolenes, and/or other functional groups associated with the various click-compatible chemistries disclosed herein.

The reaction scheme 200 features formation of oligomers comprising functional groups structurally appropriate for forming crosslinks with other similar oligomers to enable photo-activated additive manufacturing (interchangeably referred to herein as a crosslinking group or a photopolymerizable group), as well as functional groups structurally appropriate for participating in click-chemistry reactions after formation of a structure from the oligomer precursors (e.g. via photo-activated additive manufacturing). In particular, according to FIG. 2 the oligomers include acrylate groups to convey capability for crosslinking with other oligomers, but in other embodiments epoxide and/or thiol-ene groups may additionally and/or alternatively be included in the oligomer. The oligomers also include terminal alkyne groups to convey click-chemistry compatibility to the resin and resulting structures produced by additive manufacturing.

In still further embodiments different oligomers having different photo-activated additive manufacturing compatible functional groups may be included in a single-component resin. Oligomers having acrylate groups, second oligomers having epoxide groups, and third oligomers having thiol-ene groups may be included in any combination, for instance. Of course, all possible combinations of oligomers having any combination of the above functional groups may also be present, in various embodiments.

The reaction scheme 200 as shown in FIG. 2 includes reacting a compound 202 comprising a terminal alkyne, e.g. (2-hydroxyethyl)acetylene, with an azole, e.g. carbonyldiimidazole (CDI) and an amine, e.g. diethanolamine. This reaction results in formation of a precursor 204 to the single-component resin 206.

As shown in FIG. 2, the precursor 204 includes two hydroxyl groups suitable for participation in a subsequent substitution reaction to form the single-component resin 206. In particular, each hydroxyl may participate in a substitution reaction with a compound comprising a photo polymerizable group, e.g. an R-substituted acryloyl halide reagent, to impart acrylate groups onto the precursor at the hydroxyl site. The substitution reaction may be carried out in the presence of a base such as diisopropylethylamine (DIPEA) or other equivalent reagents, in various embodiments.

The resulting single-component resin 206 according to the embodiment shown in FIG. 2 is an oligomer including acrylate groups suitable for crosslinking to other oligomer molecules in the single-component resin 206 as well as a terminal alkyne group suitable for participating in click-chemistry reactions.

Exposing resin 206, which preferably includes a suitable photoinitiator, to a particular wavelength of light, e.g. light having a wavelength in the UV range, results in crosslinking of the oligomers thereof in the exposed regions of the resin 206. In one approach, where acrylate groups are present in the oligomers of the resin 206, crosslinking may proceed according to a reaction scheme 1300 as depicted in FIG. 13. Acrylate groups may interact with radicals generated by a photoinitiator, resulting in crosslinking of the oligomers of the resin 206.

In various embodiments where the single-component resin includes other functional groups suitable for crosslinking the oligomers, exposing the resin 206 to the particular wavelength of light may cause crosslinking via other reaction schemes, e.g. reaction schemes 1400 and/or 1500 as shown in FIGS. 14 and 15, respectively for epoxide groups and thiol-ene groups. Notably, the epoxide-based crosslinking reaction scheme 1400 does not rely on interaction with a radical (as is the case for the acrylate groups and thiol-ene groups) but rather is driven by cations generated by the photoinitiator. Additionally, related vinyl ether and N-vinyl carbazoles containing oligomers are also crosslinked in the presence of cations and can additionally and/or alternatively be employed as a photo polymerizable group or compound, in certain embodiments.

Figure 5:
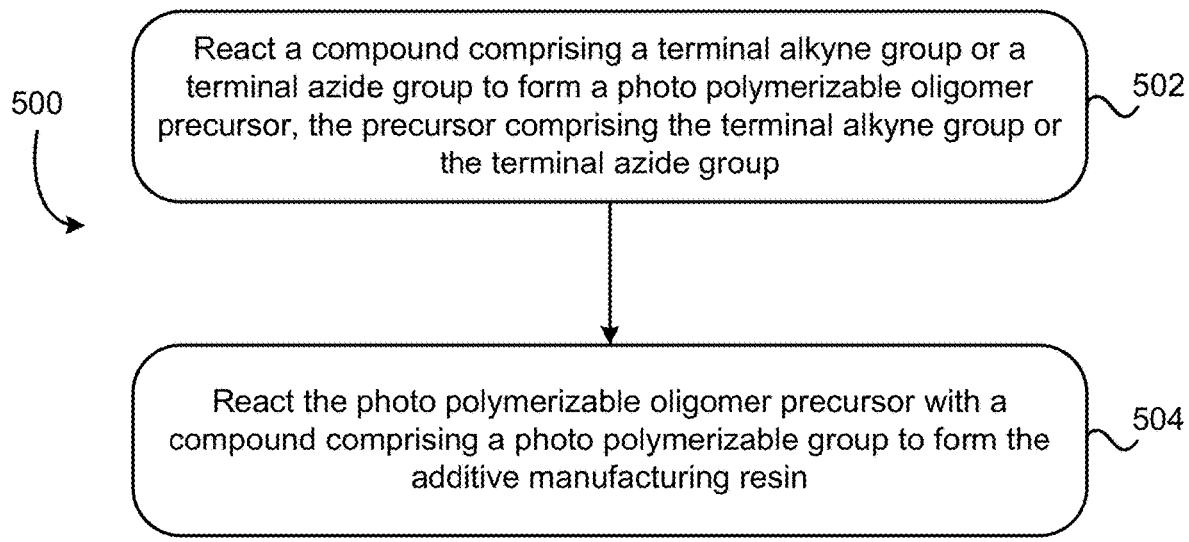
FIG. 5 is a flowchart of a method for forming a single-component resin for additively manufacturing click-chemistry compatible structures, according to various embodiments.

Accordingly, in one embodiment a method 500 of forming an additive manufacturing resin, such as a single-component resin 206, is shown in FIG. 5. The particular method 500 may vary with respect to the chemistry employed, according to different embodiments and depending on the identity of the functional groups to be included for the purpose of additive manufacturing (e.g. crosslinking) and the functional groups to be included for the purpose of conveying click-chemistry compatibility on the resulting resin.

According to the embodiment depicted in FIG. 5, method 500 includes operation 502, in which a compound comprising a terminal alkyne or a terminal azide (e.g. 202) is reacted to form a photo polymerizable oligomer precursor (e.g. 204) including the terminal alkyne or azide group.

With continuing reference to FIG. 5, method 500 also includes operation 504, where the photo polymerizable oligomer precursor is reacted with a compound comprising a photo polymerizable group (e.g. acrylate, epoxide, and/or thiol-ene groups) to form an additive manufacturing resin (e.g. 206).

As mentioned with respect to FIG. 2, in various embodiments the compound comprising the photo polymerizable group may be an R-substituted acryloyl halide reagent, e.g. acryloyl chloride or 2-methyl-2-propenoyl chloride. Of course, other suitable photo polymerizable groups such as epoxides and thiol-enes, vinyl ethers and N-vinyl carbazoles containing oligomers, as well as compounds containing the same may be used in alternative embodiments.

For instance, in one embodiment the photo polymerizable compound may be or include a polyethylene-glycol backbone functionalized with at least one photo polymerizable moiety selected from a group consisting of: acrylates, epoxides, and thiol-enes. Additionally and/or alternatively, in some embodiments the photo polymerizable compound comprises an organic backbone, e.g. a hexanediol-based backbone, a polyethylene glycol-based backbone, a vinyl-based backbone, etc. functionalized with at least one photo polymerizable moiety selected from a group consisting of: acrylates, epoxides, thiol-enes, vinyl ethers and N-vinyl carbazoles containing oligomers. As such, exemplary photo polymerizable compounds in various embodiments may include PEGDA, pentaerythritol triacrylate (PETA) EGDMA, HDDA, etc.

In more embodiments, the photo-polymerizable compounds described herein may include any moiety, structure, etc. as set forth in FIG. 16.

In more embodiments, reacting the compound comprising the terminal alkyne group or the terminal azide group to form the precursor may be performed in the presence of an azole (e.g. CDI) and an amine (e.g. diethanolamine).

In still more embodiments, reacting the precursor with the compound comprising the photo polymerizable group is performed in the presence of a base, e.g. DIPEA Of course, the foregoing exemplary method 500 contemplates forming single-component additive manufacturing resins where the photo polymerizable group leveraged for additive manufacturing is one or more acrylate functional groups, and a terminal alkyne provides click-chemistry compatibility. In other embodiments, the method 500 may employ different chemistry than shown in the reaction scheme 200 in order to accommodate azide-based click-chemistry compatibility, and/or epoxide or thiol-ene-based crosslinking and additive manufacturing.

In another approach, a simplified reaction scheme 300 for forming a dual-component resin for additively manufacturing click-chemistry compatible structures is shown in FIG. 3. As will be explained in further detail below, dual-component resins are advantageously characterized by including a reactive diluent monomer, which may have the click-chemistry compatible functional group thereof optionally and preferably protected to as to control the ability of the resulting resin and structures formed therewith to participate in click-chemistry or other reactions. In particularly preferred approaches, the protection of the click-chemistry compatible group prevents this group from reacting with other components of the resin during the additive manufacturing process, e.g. from reacting with radicals or cations generated by a photoinitiator.

To be clear, reactive diluent monomers and/or oligomers as described herein need not be functionalized with protecting groups to be effective in click-chemistry or other synthesis schemes disclosed herein. However, preferred embodiments of click-chemistry compatible structures include a protective group functionalized to the functional group that participates in the cycloaddition or other synthesis reaction. Particularly in the case of alkynes, protection advantageously improves the degree to which a formed product is functionalized on surfaces thereof by preventing the alkynes from polymerizing during the fabrication process.

As discussed herein, the term "dual-component" refers to the existence of two components that participate in the photo-activated additive manufacturing reaction (e.g. as shown in FIGS. 13-15, and described in further detail below). In further embodiments, dual-component resins may include multiple different types of functional group(s) suitable for photo-activated additive manufacturing, such as acrylates (shown in FIG. 3), epoxides, thiol-enes, and/or any other suitable functional groups associated with different click-chemistry schemes of the various types disclosed herein.

Those having ordinary skill in the art will appreciate, upon reading the instant disclosures, that the resin according to various embodiments may include other materials, such as photoactivators, photoabsorbers, photoinitiators, solvents (e.g. dimethylformamide, dimethylacetamide, tetrahydrofuran (THF), toluene, acetone, etc.), viscosity modifying agents (such as stabilizers, binders, surfactants, etc.), and/or pore-forming compounds (e.g. silica nanoparticles, uncrosslinked polystyrene beads, suitable salts such as sodium chloride, etc.), and/or other suitable materials that would be understood by a skilled artisan upon reading the instant descriptions.

The reaction scheme 300 features formation of reactive diluents comprising functional groups structurally appropriate for forming crosslinks with other similar reactive diluents and/or crosslinker components (e.g. PEGDA, EGDMA, PETA, HDDA, etc.) to enable photo-activated additive manufacturing. The reactive diluents also include functional groups structurally appropriate for participating in click-chemistry reactions after formation of a structure from the reactive diluent and crosslinker components via photo-activated additive manufacturing.

In particular, according to FIG. 3 the reactive diluents include acrylate groups to convey capability for crosslinking with other oligomers, but in other embodiments epoxide and/or thiol-ene groups may additionally and/or alternatively be included in the reactive diluent. The reactive diluent also includes a terminal alkyne group for the purpose of providing click-chemistry compatibility to the dual-component resin 306. Preferably, and again as shown in FIG. 3, the reactive diluent features a protecting group (e.g. trimethylsilane, TMS) functionalized to the terminal alkyne in order to prevent the terminal alkyne participating in radical interactions or other reactions occurring during the crosslinking additive manufacturing process. Protecting groups and techniques for deprotecting click-chemistry compatible compounds/groups as described herein will be discussed in further detail below regarding FIGS. 7A-7B.

In still further embodiments different reactive diluents having different photo-activated additive manufacturing compatible functional groups may be included in a dual-component resin. Reactive diluents having acrylate groups, second reactive diluents having epoxide groups, and third reactive diluents having thiol-ene groups may be included in any combination, for instance. Of course, all possible combinations of reactive diluents having any combination of the above functional groups may also be present, in various embodiments.

The reaction scheme 300 as shown in FIG. 3 includes reacting a compound 302 comprising a terminal alkyne (e.g. (2-hydroxyethyl)acetylene) with a protecting reagent, i.e. a compound such as TMS, e.g. trimethylsilane chloride (TMSCl), and an organolithium reagent (e.g. n-butyllithium (nBuLi)). The resulting compound can then be treated with an acid solution, preferably a strong acid such as hydrochloric acid.

The resulting protected reactive diluent precursor 304 features a terminal alkyne functionalized with a protecting group, TMS as shown in FIG. 3. The protected reactive diluent precursor 304 also includes a hydroxyl moiety suitable for participating in a substitution reaction with a compound featuring a functional group suitable for photo-activated additive manufacturing, e.g. a crosslinking group such as an acrylate, epoxide, and/or thiol-ene functional group. As shown in FIG. 3, the compound utilized for this purpose is an R-substituted acryloyl halide. The R— group may be a functional group selected from hydrogen, methyl, etc. in various embodiments.

Reacting the protected reactive diluent precursor 304 with the compound having the crosslinking group (also referred to as a photo-polymerizable group) in the presence of DIPEA to form a protected reactive diluent, one of the two components of the dual component resin 306. Where the compound having the crosslinking group(s) is a 2-acryloyl halide or R-substituted derivative thereof, the halide acts as a leaving group and the compound binds to the hydroxyl terminus of the protected reactive diluent precursor 304, according to the reaction scheme 300 shown in FIG. 3.

After forming the protected reactive diluent according to reaction scheme 300 as shown in FIG. 3, the protected reactive diluent may be combined with a crosslinker component, e.g. PEGDA, EGDMA, PETA, HDDA, etc. as would be understood by a person having ordinary skill in the art upon reading the present descriptions, in order to complete the dual-component additive manufacturing resin 306.

Of course, in various approaches other materials may be included in such dual-component additive manufacturing resins, e.g. photoinitiators, photoabsorbers, etc. as disclosed herein and as would be appreciated by a person having ordinary skill in the art upon reading the present disclosures.

The resulting dual-component resin 306 according to the embodiment shown in FIG. 3 includes a protected reactive diluent monomer including acrylate, epoxide, and/or thiol-ene groups suitable for crosslinking to other protected reactive diluent monomers in the dual-component resin 306 as well as a terminal alkyne group suitable for participating in click-chemistry reactions. In various embodiments the terminal alkyne may be replaced with a terminal azide, as shown in FIG. 4. The dual-component resin also includes a crosslinker such as PEGDA, EGDMA, PETA, HDDA, etc. having functional groups such as acrylates, epoxides, and/or thiol-enes for participating in polymerization, e.g. via crosslinking, during photo-activated additive manufacturing. The polymerization/crosslinking reaction in the case of a dual-component resin 306 also results in the incorporation of the dilutive reactant with the click-chemistry compatible functional group(s) into the polymer and thus the structures produced via additive manufacturing. Suitable processes for forming structures functionalized with click-chemistry compatible functional groups will be described in further detail below regarding FIG. 10, and techniques for further functionalizing such structures will be described in further detail below with respect to FIG. 11, according to several exemplary embodiments.

Exposing the resin 306, which preferably includes a suitable photoinitiator, to a particular wavelength of light, e.g. light having a wavelength in the UV range, results in crosslinking of the oligomers thereof in the exposed regions of the resin 306. In one approach, where acrylate groups are present in the oligomers of the resin 306, crosslinking may proceed according to a reaction scheme 1300 as depicted in FIG. 13. Acrylate groups may interact with radicals generated by the photoinitiator, resulting in crosslinking of the oligomers of the resin 306.

In various embodiments where the dual-component resin includes other functional groups suitable for crosslinking the oligomers, exposing the resin 306 to the particular wavelength of light may cause crosslinking via other reaction schemes, e.g. reaction schemes 1400 and/or 1500 as shown in FIGS. 14 and 15, respectively for epoxide groups and thiol-ene groups. Notably, the epoxide-based crosslinking reaction scheme 1400 does not rely on interaction with a radical (as is the case for the acrylate groups and thiol-ene groups) but rather is driven by cations generated by the photoinitiator in response to exposure to light of a particular wavelength.

Figure 6:
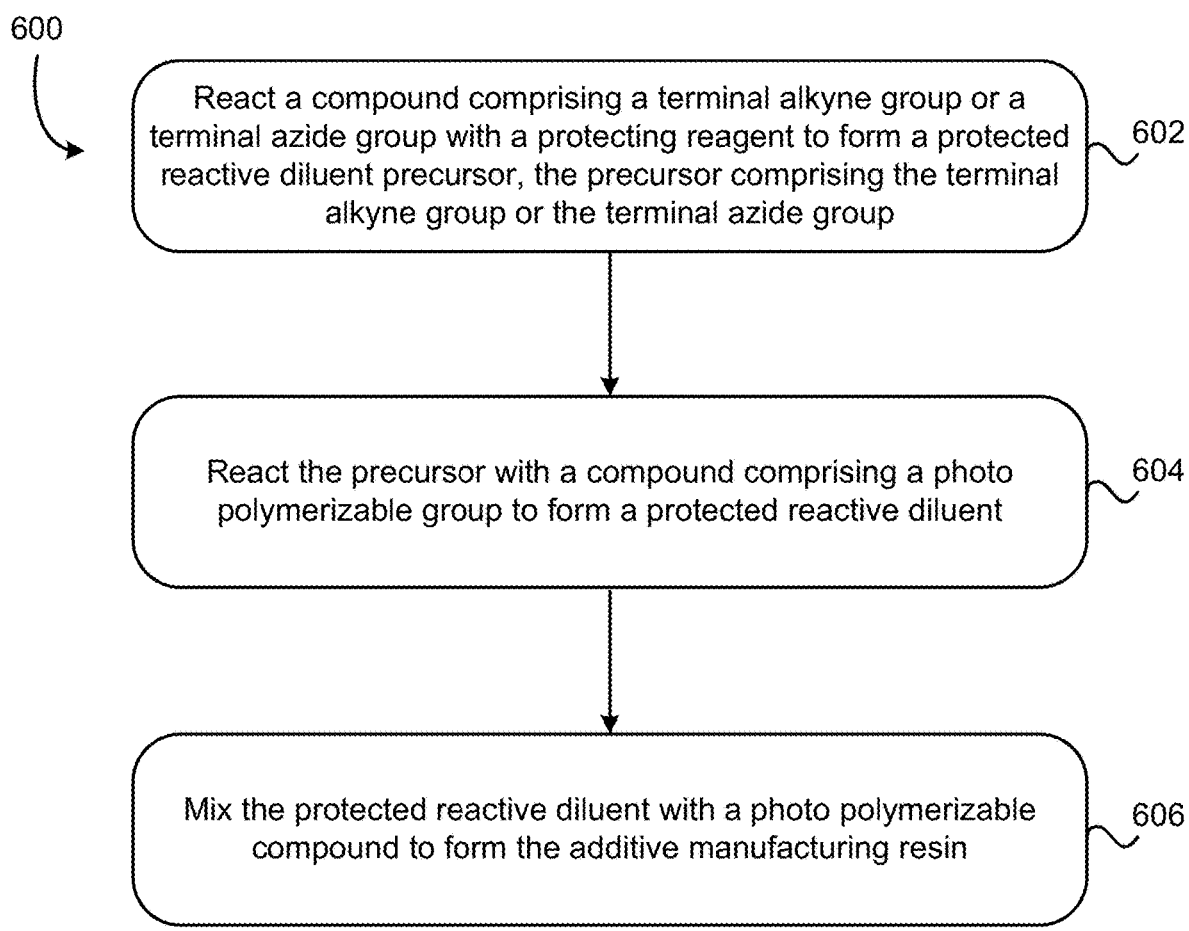
FIG. 6 is a flowchart of a method for forming a dual-component resin for additively manufacturing click-chemistry compatible structures, according to various embodiments.

Accordingly, in one embodiment a method 600 of forming an additive manufacturing resin, such as a dual-component resin 306, is shown in FIG. 6. The particular method 600 may vary with respect to the chemistry employed, according to different embodiments and depending on the identity of the functional groups to be included for the purpose of additive manufacturing (e.g. crosslinking) and the functional groups to be included for the purpose of conveying click-chemistry compatibility on the resulting resin.

As shown in FIG. 6, method 600 includes operation 602, in which a compound comprising a click-chemistry compatible functional group such as a terminal alkyne or a terminal azide group (e.g. 302) is reacted with a protecting reagent to form a protected reactive diluent precursor (e.g. 304) that includes the click-chemistry compatible functional group (e.g. terminal alkyne or terminal azide group).

With continuing reference to FIG. 6, method 600 includes operation 604, where the precursor formed in operation 602 is reacted with a compound comprising a photo polymerizable group in order to form a protected reactive diluent.

Further still, in operation 606 of method 600 the protected reactive diluent is mixed with a photo polymerizable compound, e.g. a crosslinker as shown in FIG. 3, to form an additive manufacturing resin. The mixture may be created using any suitable technique, and may include one or more such crosslinkers, preferably the crosslinkers have a suitably low viscosity to allow rapid additive manufacturing in a layer-wise fashion.

In various embodiments, method 600 may include any number of additional or alternative features, operations, may be performed under specified conditions, etc. as would be appreciated by a person having ordinary skill in the art upon reading the present disclosure.

For instance, in one embodiment the photo polymerizable compound may be or include a polyethylene-glycol backbone functionalized with at least one photo polymerizable moiety selected from a group consisting of: acrylates, epoxides, and thiol-enes. Additionally and/or alternatively, the photo polymerizable compound comprises a hexanediol backbone functionalized with at least one photo polymerizable moiety selected from a group consisting of: acrylates, epoxides, and thiol-enes. As such, the photo polymerizable compound in various embodiments may include PEGDA, EGDMA, PETA, HDDA, etc. In more embodiments, the photo-polymerizable compounds described herein may include any moiety, structure, etc. as set forth in FIG. 16.

In more embodiments, the protecting reagent may include a protecting group selected from a group consisting of: a trimethylsilyl, a triethylsilyl, a t-butyl dimethylsilyl, a triisopropylsilyl, and a 2-(2-hydroxypropyl)alkyne, e.g. as shown in FIG. 7A. As further shown in FIG. 7A, and according to various embodiments the protecting group may subsequently be removed (i.e. the click-chemistry compatible group may be deprotected) by exposing the protecting groups to conditions such as fluoride, silver nitrate, alkali conditions (e.g. refluxing sodium hydroxide).

For instance, in preferred embodiments where the protecting group is present during formation of three-dimensional structures via photo-activated additive manufacturing, and even after such manufacturing the protecting group remains functionalized to the click-chemistry compatible group. Accordingly, deprotection may involve submerging or washing the structure in a solution of one or more of the foregoing deprotecting agents, e.g. a dilute fluoride solution, silver nitrate solution, alkali solution, etc. as would be understood by a person having ordinary skill in the art upon reading the present disclosures.

Figure 12:
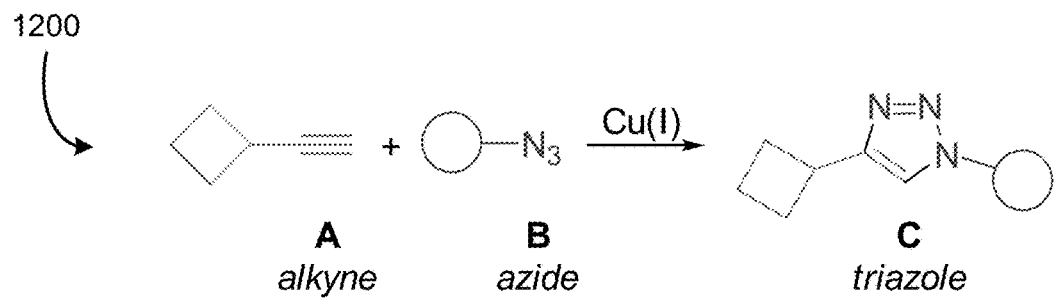
FIG. 12 depicts a simplified reaction scheme for copper-catalyzed alkyne azide cycloaddition (CuAAC) click chemistry, according to one embodiment.

As shown in FIG. 7B, the materials generally disclosed herein as suitable for inclusion in additive manufacturing resins, and particularly the protective dilutive reactants synthesized according to a reaction scheme 300 as shown in FIG. 3 may be characterized by a structure including a polymerizable group, e.g. an acrylate, epoxide, and/or thiol-ene, a linker (see e.g. FIG. 16), a click-chemistry compatible group, e.g. a terminal alkyne or azide, and a protecting group functionalized on the click-chemistry compatible group. In order to further functionalize the structures formed, e.g. by additive manufacturing as alluded-to above, the protecting group may be removed, as further depicted in FIG. 7B. Thereafter, further functionalization may be carried out via a click chemistry reaction, such as a CuAAC reaction 1200 as shown in FIG. 12. Of course, other click chemistry reactions and schemes disclosed herein may be employed without departing from the scope of the presently disclosed inventive concepts.

Again, it should be understood that although the click-chemistry compatible functional groups depicted in FIGS. 7A and 7B are terminal alkynes, in various embodiments terminal azides may be substituted for the terminal alkyne without departing from the scope of the inventive concepts discussed herein. Similarly, any equivalent click-chemistry compatible functional group that would be appreciated by a skilled artisan upon reading the present disclosures may be employed, and equivalent protecting groups therefor, without departing from the scope of the presently described inventive concepts.

In more embodiments of method 600, reacting the compound comprising the terminal alkyne group or a terminal azide group with the protecting reagent attaches a protecting group to the terminal alkyne group or the terminal azide group, and the reaction may be performed in the presence of an organolithium reagent (e.g. n-butyllithium) and an acid (e.g. a strong acid such as hydrochloric acid).

Further still, according to various embodiments of method 600, reacting the precursor with the compound comprising the photo polymerizable group is performed in the presence of a base, such as DIPEA.

While the embodiments described above are characterized by compounds including a terminal alkyne for the purpose of conveying click-chemistry compatibility to the resulting resins and structures, it will be appreciated that the presently disclosed inventive concepts are inclusive of embodiments where the functional group(s) included to convey click-chemistry compatibility include terminal azides, in addition or alternatively to terminal alkynes.

For instance, a reaction scheme 400 as shown in FIG. 4 depicts a simplified synthetic pathway suitable for forming compounds having terminal azides as well as functional groups suitable for crosslinking to enable photo-activated additive manufacturing. As shown in FIG. 4, the reaction scheme 400 results in synthesis of a compound having an acrylate and a terminal azide. Of course, other functional groups suitable for photo-activated additive manufacturing, such as epoxide groups and/or thiol-ene groups (see e.g. FIGS. 14 and 15) may be included in any combination in compounds also having terminal alkynes and/or azides and thus provide both click-chemistry compatibility and photo-activated additive manufacturing capability, in various embodiments.

Returning now to FIG. 7A, in various embodiments protecting groups may be functionalized to the click-chemistry compatible functional groups of the presently disclosed inventive compounds. For example, suitable protecting groups may comprise or be a trialkylsilyl group, e.g. trimethylsilyl (TMS), triethylsilyl (TES), t-butyldimethylsilyl (TBS), triisopropylsilyl (TIPS), and/or a 2-(2-hydroxypropyl) group.

Similarly, and as shown particularly in FIG. 7B, the protecting groups may be removed (i.e. deprotection may be accomplished) using suitable chemistry that would be appreciated by a skilled artisan reading the present disclosures and depending on the identity of the protecting group. For instance, where the protecting group comprises or is a trialkylsilyl group, e.g. trimethylsilyl (TMS), triethylsilyl (TES), t-butyldimethylsilyl (TBS), or triisopropylsilyl (TIPS), deprotection may include treatment with a fluoride, silver nitrate, and/or alkali solution. Where the protecting group comprises or is not a trialkylsilyl, e.g. a 2-(2-hydroxypropyl) group, deprotection may include refluxing the compound with a strong base such as sodium hydroxide, potassium hydroxide, etc. Of course, other deprotection chemistries may be employed without departing from the scope of the presently disclosed inventive concepts, e.g. using equivalents to the above schemes that would be appreciated by a person having ordinary skill in the art upon reading the present descriptions.

With continuing reference to FIG. 7B, click-chemistry compatible components of additive manufacturing resins (especially those components which comprise the dilutive reactant component of a dual-component resin) may be structurally characterized by including a polymerizable (or crosslinking) group such as an acrylate, thiol-ene, epoxide, etc. and a click-chemistry compatible group such as a terminal alkyne or a terminal azide (optionally protected) joined by a linker chain. Various embodiments of suitable linkers are shown in FIG. 16, and may generally include aliphatic groups, polyethylene groups, aromatic groups, dimethylsiloxane groups, esters, amides, amines, ethers, ureas, carbamates, carbonates, and/or sulfones. These linkers may be characterized by being R-substituted, where R may include methyl, hydrogen, alkyl and/or aryl moieties in various approaches.

Figure 8A:
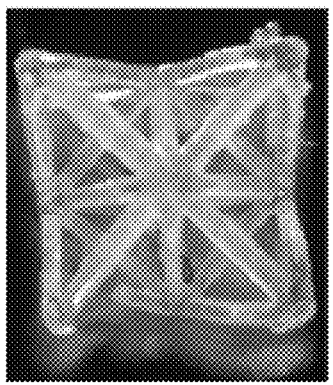
FIGS. 8A and 8B depict embodiments of a three-dimensional structure formed by additive manufacturing as disclosed herein. The structure has surfaces which are functionalized to be click-chemistry compatible, and in FIG. 8B the structure is further functionalized via click chemistry to incorporate a fluorescing group onto the surfaces of the structure.
Figure 8B:
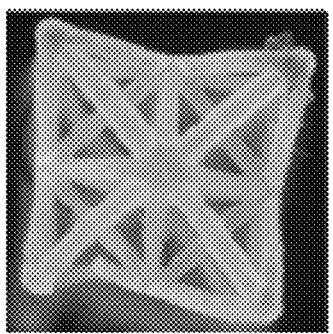

Turning now to FIGS. 8A-8B, and as alluded to previously, the additive manufacturing resins described above may be utilized in an additive manufacturing process to form unique structures with precisely defined features, e.g. on the scale of several hundred nanometers in preferred embodiments. As depicted in FIGS. 8A-8B, an octahedral truss has been formed according to one embodiment using materials and techniques as described herein. The same truss is shown in both FIGS. 8A and 8B, while the truss as depicted in FIG. 8B is exposed to ultraviolet light in order to cause an organic additive (coumarin) functionalized thereto via click-chemistry to fluoresce. The structures shown in FIGS. 8A and 8B were created as a proof-of-principle demonstration of the ability to incorporate click-chemistry compatible groups into additive manufacturing resins, create click-chemistry compatible structures via additive manufacturing using such resins, and functionalize the resulting structures via click-chemistry.

Accordingly, in various embodiments a composition of matter consistent with the inventive concepts disclosed herein includes a three-dimensional structure comprising photo polymerized and/or crosslinked molecules, where surfaces of the three-dimensional structure are functionalized with one or more click-chemistry compatible functional groups. In various embodiments, and depending on the nature of the additive manufacturing resin utilized to form the three-dimensional structure, the click-chemistry compatible functional groups may optionally but preferably be protected with a protecting group or reagent. The protecting group or reagent may be removed (i.e. the structure may be deprotected) using appropriate chemistry as described in further detail below to allow click-chemistry based functionalization of the structure, or at least surfaces thereof.

The click-chemistry compatible functional groups are preferably configured to engage in a click-chemistry reaction as disclosed herein, particularly preferably a copper-catalyzed azide-alkyne cycloaddition (CuAAC) reaction, e.g. via inclusion of terminal alkynes, azides, or both. Thus, in more embodiments, at least some of the click-chemistry compatible functional groups are structurally characterized by conversion into triazoles via the CuAAC reaction, as discussed in further detail below regarding FIG. 9.

More preferably, at least some of the click-chemistry compatible functional groups are protected by one or more protecting groups, such as a functional group selected from a group consisting of: a trimethylsilyl, a triethylsilyl, a t-butyl dimethylsilyl, a triisopropylsilyl, and a 2-(2-hydroxypropyl) group.

In one embodiment, photo polymerizable and/or crosslinking precursor compounds preferably include functional groups that are selected from acrylates, epoxies, thiol-enes, and/or other click-compatible chemistries as set forth herein. One or more of the foregoing functional groups may be present in various implementations. Accordingly, the photo polymerized molecules of the composition of matter may preferably include one or more photo polymerized moieties formed from polymerizing precursor compounds having photo polymerizable group(s) selected from: acrylates, epoxies, and thiol-enes.

In one embodiment, at least some of the click-chemistry compatible functional groups are functionalized with an additive selected from a group consisting of an antibiotic and an antibacterial compound, such as silver ions and/or fimbrolides.

The composition of matter may optionally be functionalized such that at least some of the click-chemistry compatible functional groups form a self-assembled monolayer (SAM), and the SAM may be or include a click-chemistry compatible polymer such as an azide or alkyne terminated poly(polyethylene glycol)) methacrylate, and/or derivatives thereof.

Further still, at least some of the click-chemistry compatible functional groups may be functionalized with silica dioxide nanoparticles in embodiments configured to provide tunable wettability to the structure.

The click-chemistry compatible functional groups may additionally or alternatively be functionalized to render the surfaces of the three-dimensional structure hydrophobic, or hydrophilic, e.g. via functionalization with compounds having hydrophobic and/or hydrophilic moieties. In various approaches certain surfaces of the structure may be rendered hydrophobic, while other surfaces may be rendered hydrophilic.

Further still, some or all of the click-chemistry compatible functional groups may be functionalized with a pharmacophore.

The three-dimensional structure may be solid throughout a bulk thereof, or may be porous in certain portions or throughout the bulk.

The three-dimensional structure, particularly in embodiments where formation thereof is achieved via projection microstereolithography, may be characterized by features having a size in a range from several hundred nanometers to several hundred microns. Of course, other feature sizes and ranges thereof as disclosed herein may be employed without departing from the scope of the presently disclosed inventive concepts.

Figure 9:
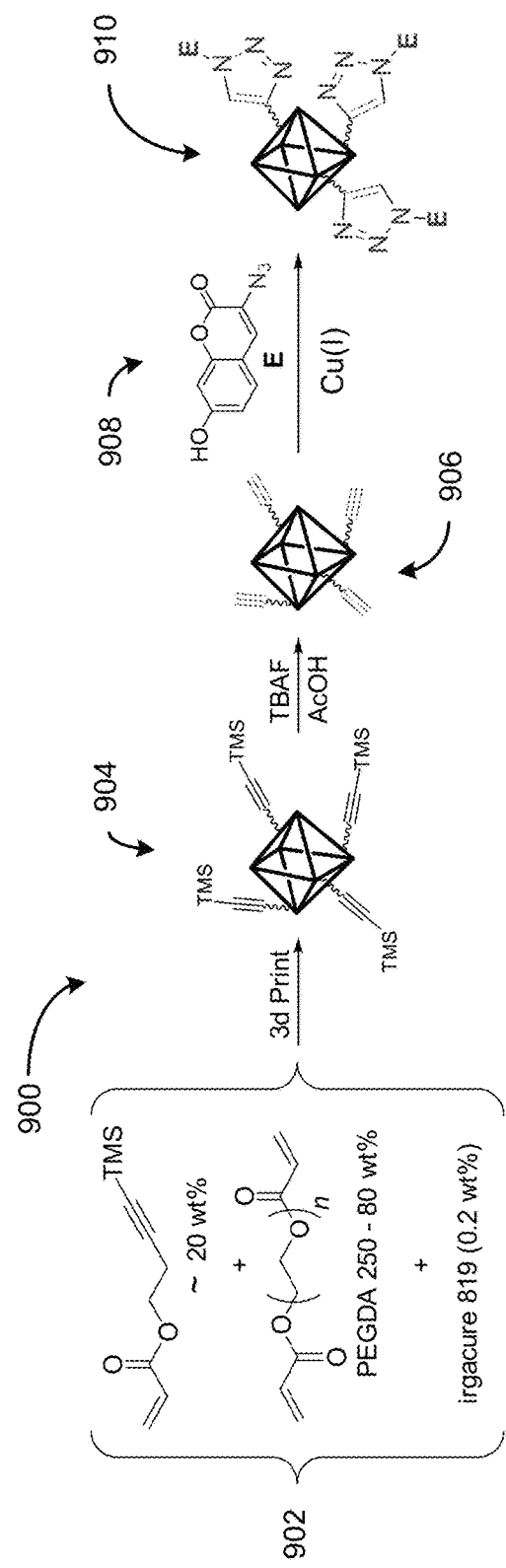
FIG. 9 depicts a simplified reaction scheme for forming the structures as shown in FIGS. 8A and 8B, in one embodiment.

A simplified process 900 for forming the structures shown in FIGS. 8A-8B is shown according to one embodiment in FIG. 9. In particular, the process 900 involves forming (e.g. via additive manufacturing techniques such as projection microstereolithography) a three-dimensional structure 904 from an additive manufacturing resin 902. As shown in FIG. 9, the resin 902 employed to form the octahedral truss shown in FIGS. 8A and 8B is a dual-component resin (e.g. 306) and includes a photoactivator (e.g. irgacure 819), a protected click-chemistry compatible component and a crosslinker component (e.g. PEGDA 250). Although the formation process referenced by FIG. 9 comprises photo activated additive manufacturing, any suitable formation process that would be appreciated by skilled artisans upon reading the present disclosure may be utilized without departing from the scope of the presently disclosed inventive concepts.

The formation process shown in FIG. 9 results in a three-dimensional structure 904 such as the octahedral truss shown in FIGS. 8A-8B, where surfaces of the structure 904 are characterized by functionalization with a click-chemistry compatible group, e.g. a terminal alkyne or azide, which is protected, e.g. with TMS. The entire surface area of the structure 904 may be so functionalized, or selected portions thereof may be functionalized, in various embodiments. The bulk of the structure 904 may comprise crosslinked molecules formed from components of the resin 902, and optionally other resin(s).

For instance, the formation process may include using different resins at different points of time while forming the structure 904, some of which may include a click-chemistry compatible component, and others of which may omit such click-chemistry compatible components. In more approaches, a digital mask may define select portions of the resin 902 to cure (e.g. via crosslinking) and some portions may correspond to a region within the resin bath that include click-chemistry compatible components, while other regions may not include such click-chemistry compatible components.

A fluidics system may facilitate such selective presence of click-chemistry compatible components in different regions of a precursor bath (e.g. 116), e.g. by flowing different resin compositions into a chamber at different times throughout the formation process, and/or by creating standing channels in different regions of the chamber.

After forming the structure, the click-chemistry compatible groups may be deprotected to form a deprotected click-chemistry compatible structure 906. Deprotection may be accomplished by washing surfaces of the structure 904 with a solution of deprotecting agent (e.g. as discussed above). As depicted in FIG. 9, the deprotecting agent comprises a solution of dilute tetra-n-butylammonium fluoride in acetic acid. The resulting deprotected click-chemistry compatible structure 906 is thus ready for functionalization with a suitable organic additive via a click-chemistry reaction. Organic additives may include any molecule including a click-chemistry compatible functional group (e.g. alkyne, azide, and/or preferably a terminal alkyne or azide). This flexibility provides very broad applicability of the presently disclosed inventive concepts in terms of functionalizing custom-designed three-dimensional structures for a variety of purposes, as discussed further below.

Referring again to FIG. 9 and process 900, the deprotected click-chemistry compatible structure 906 may be functionalized with coumarin 908 (compound E) by placing the coumarin 908 in proximity to the deprotected click-chemistry compatible structure 906 in the presence of a catalyst. In various embodiments, the catalyst may include one or more catalysts selected from a group consisting of copper (I), ruthenium, silver, gold, iridium, nickel, zinc, and lanthanum.

This results in a CuAAC reaction (see process 1200 of FIG. 12) whereby the terminal alkyne of the deprotected click-chemistry compatible structure 906 reacts with the azide group of the coumarin 908 to cause cycloaddition of coumarin 908 to the structure 906, resulting in a functionalized structure 910. FIGS. 8A and 8B demonstrate this structure was the result of the CuAAC reaction, since coumarin 908 is not fluorescent under UV light, but the resulting structure 910 exhibited fluorescence (via the triazole groups) as expected.

In various embodiments, the terminal alkyne and azide may be present on the structure 906, the organic additive (e.g. coumarin 908) interchangeably. Other click-chemistries and suitable functional groups therefor that would be understood as equivalent to those shown in FIG. 9 may be employed without departing from the scope of the presently described inventive concepts.

Figure 10:
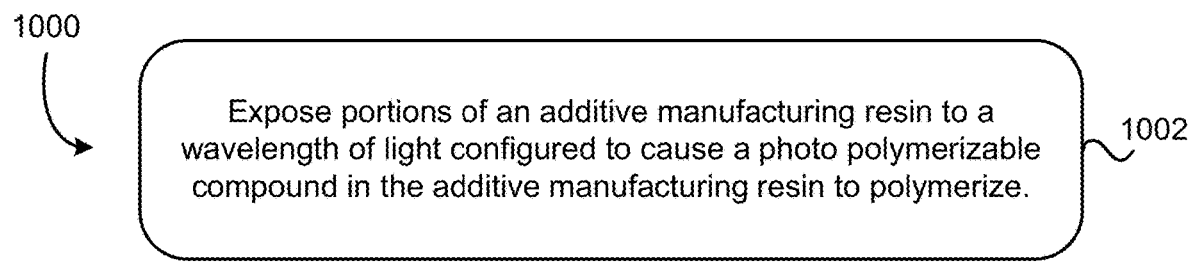
FIG. 10 is a flowchart of a method for additively manufacturing click-chemistry compatible structures as disclosed herein, according to one approach.

Accordingly, and with reference to FIG. 10, in various embodiments a method 1000 of forming a click-chemistry compatible structure includes, in operation 1002, exposing, e.g. according to a three-dimensional pattern such as described above regarding FIG. 1, select portions of an additive manufacturing resin to a wavelength of light configured to cause a photo polymerizable compound such as a crosslinking agent in the additive manufacturing resin to polymerize (e.g. crosslink), thereby rendering the exposed portions of the additive manufacturing resin into a solid layer of the click-chemistry compatible structure. Preferably, the additive manufacturing resin comprises at least one compound having a click-chemistry compatible functional group and more preferably the photo polymerizable compound includes click-chemistry compatible functional group (s).

The method 1000 may optionally include any combination of additional operations, features, etc. as disclosed herein without departing from the scope of the present disclosure. In one approach, the portions of the additive manufacturing resin exposed to the wavelength of light are defined according to a predetermined mask.

The method 1000 in other approaches may include submerging the solid layer of the click-chemistry compatible structure in the additive manufacturing resin; and exposing either the portions of the additive manufacturing resin or other portions of the additive manufacturing resin to the wavelength of light to form a second layer of the click-chemistry compatible structure. Again, the exposure may be performed according to a predefined, preferably three-dimensional, pattern.

The method 1000 in still other approaches may include iteratively repeating the submerging and the exposing to form a plurality of layers of the click-chemistry compatible structure according to a predetermined three-dimensional pattern.

The wavelength of light may be selected based on an excitation wavelength of a photoinitiator in the resin, and in some approaches (such as shown in FIG. 9) may be a wavelength in the ultraviolet (UV) range. In various embodiments, the method 1000 may cause molecules to polymerize and/or crosslink according to reactive schemes 1300, 1400, and/or 1500 as shown respectively in FIGS. 13-15. The polymerization and/or crosslinking preferably causes the exposed portions of a resin/precursor bath to precipitate into a layer of solid, optionally porous material (e.g. where the resin includes pore-forming materials as described herein, such as salts, uncrosslinked polystyrene beads, silica nanoparticles, etc.).

Figure 11:
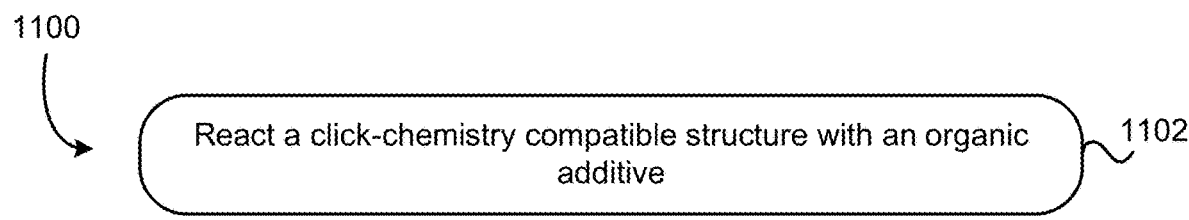
FIG. 11 is a flowchart of a method for functionalizing click-chemistry compatible structures as disclosed herein, according to one embodiment.

Referring now to FIG. 11, a method 1100 of functionalizing a click-chemistry compatible structure may proceed according to operation 1102, in which a click-chemistry compatible structure is reacted with an organic additive. The click-chemistry compatible structure reacted with the organic additive includes a plurality of click-chemistry compatible molecules each independently having one or more click-chemistry compatible functional groups (e.g. terminal alkynes and/or azides, in one embodiment). The click-chemistry compatible molecules are functionalized on surfaces of the structure; while the organic additive includes at least some compound(s) each independently having one or more click-chemistry compatible functional groups other than the click-chemistry compatible functional groups of the molecules functionalized on the surfaces of the structure (e.g. the other of the terminal alkyne or azide). Furthermore, the click-chemistry compatible molecules functionalized on the surfaces of the click-chemistry compatible structure are structurally configured to react with the one or more click-chemistry compatible functional groups of the organic additive and thereby attach the organic additive to the click-chemistry compatible structure via the click-chemistry compatible molecules functionalized on the surfaces of the structure.

In one embodiment, for instance, the functional groups functionalized on the surfaces of the click-chemistry compatible structure comprise one component of a click-chemistry compatible reaction (e.g. terminal alkyne or terminal azide for a CuAAC reaction) while the functional groups of the organic additive comprise the other component of the click-chemistry compatible reaction (e.g. the other of the terminal alkyne or terminal azide). In some embodiments, functional groups forming both components of the click-chemistry compatible reaction may be included in molecules functionalized to the surfaces of the structure as well as included in the organic additive. Of course, when click chemistry proceeds according to other schemes mentioned herein or as would be understood by a person having ordinary skill in the art upon reading the present disclosures, the respective functional groups may include corresponding components of such other schemes so as to enable click-chemistry functionalization of the structure with moieties present in the organic additive or additives.

The method 1100 may include any number or combination of alternative and/or additional operations, features, etc. shown in FIG. 11, in various embodiments. For instance, and according to preferable CuAAC reactions, the functionalization reaction may optionally be performed in the presence of a catalyst such as copper (I). As will be appreciated by skilled artisans upon reading the present disclosure, different functionalizations may be carried out for different portions of the structure, e.g. by selectively applying different organic additives and/or catalysts to different portions of the structure, by using different types of click-chemistry on different portions of the structure, etc. in various embodiments. Accordingly, the catalyst may include one or more materials selected from a group consisting of copper (I), ruthenium, silver, gold, iridium, nickel, zinc, and lanthanum. In some click chemistries, catalysts may be unnecessary to accomplish the click reaction.

Even more preferably, the click-chemistry compatible structure comprises a compound selected from a group consisting of: acrylates, epoxides and thiol-enes, which advantageously allows for projection microstereolithography to be utilized to form the structure, as discussed above. Of course, formation techniques and procedures other than projection microstereolithography may be implemented, particularly photo polymerization-based techniques and procedures, without departing from the scope of the presently disclosed inventive concepts.

To confer useful added functionality to the functionalized structure, the organic additive in various embodiments may be or include an antibiotic and/or an antibacterial compound, such as silver ions and/or fimbrolides.

The method 1100 may additionally and/or alternatively include functionalizing at least some of the functional groups functionalized on the surfaces of the click-chemistry compatible structure to form a self-assembled monolayer (SAM). The SAM may be or include a compound such as an azide- or alkyne-terminated poly(polyethylene glycol)) methacrylate derivative, e.g. poly(polyethyleneglycol) methyl ether methacrylate.

In more embodiments, and to convey improved wettability of the structure's surfaces, the organic additive may include or be tethered to silica dioxide nanoparticles.

The click-chemistry reaction may optionally include functionalizing at least some of the functional groups on the surfaces of the click-chemistry compatible structure, e.g. in order to render the surfaces of the click-chemistry compatible structure hydrophobic, in other embodiments. Additionally and/or alternatively, the method 1100 may include functionalizing at least some of the functional groups functionalized on the surfaces of the click-chemistry compatible structure to render the surfaces of the click-chemistry compatible structure hydrophilic.

Further still, the organic additive may be or comprise a pharmacophore to convey pharmacological utility to certain embodiments.

Applications/Uses

According to various embodiments, organic additives may be reacted with the functionalized structures to convey anti-corrosive, anti-microbial, anti-fouling, tunable wettability, and/or pharmacophore delivery characteristics to the structures.

Regarding anti-corrosive surface modification, in one exemplary approach triazoles, one product of copper-catalyzed azide-alkyne cycloaddition (CuAAC), are nitrogen-containing heterocyclic compounds that exhibit desirable corrosion inhibition for metals and alloys against acid and alkaline media. As such, triazoles and related compounds are industrial important materials for coating purposes and may be formed on surfaces of the functionalized structure to provide anti-corrosive characteristics thereto.

In other approaches, antimicrobial agents can range from known antibiotics to silver ions and can be used to prepare hygienic surfaces. Many antibiotics, for instance, are organic compounds that are thus amenable to manipulation through click chemistry such as CuAAC reactions.

Similar to antimicrobial functionalization, in some embodiments click chemistry such as CuAAC reactions can be employed to yield self-assembling monolayers (SAM)

coatings that may inhibit the adhesions of proteins and/or other biological organisms. For instance, in one example hydrophilic an alkyne- or azide-terminated poly (polyethylene glycol) methacrylate polymer, and/or derivative(s) thereof, may be utilized in a CuAAC reaction to form a SAM on surfaces of the functionalized structures disclosed herein, and such coatings may prevent or significantly reduced the absorption of proteins such as bovine serum albumin (BSA).

Regarding wettability control, the capability/tendency for liquid(s) to maintain contact with a solid surface may be selectively controlled/tuned via click chemistry. For example, additively manufactured parts may be functionalized to exhibit either hydrophobic or hydrophilic surfaces, e.g. through surface chemistry modification. In one embodiment, the structures discussed herein may have silica dioxide nanoparticles attached thereto using CuAAC, thereby improving wettability of the material functionalized surfaces.

Turning now to pharmacophores, CuAAC can be employed as a means to quickly and reliable append a pharmacologically relevant molecule to the surface of a material. More advanced systems may optionally feature a biodegradable and/or bio-activated linkage between the pharmacophore and the CuAAC reactive groups, allowing the pharmacophore to be selectively released. For instance, an additively manufactured stint may be coated with an antibiotic, anti-cancer drug, and/or anti-cholesterol drug, such that the drug is slowly released over time when the stint is implanted in the patient. In another example, an additively manufactured produced porous substrate may be formed and configured to allow for biomedical applications, such as bone growth, in which the surface could be modified through CuAAC, e.g. to enhance cell adhesion.

Various illustrative and exemplary embodiments of suitable surface modifications in different applications or fields of use have been set forth above by way of example. It should be understood that embodiments of structures as described herein may include one or more of the foregoing exemplary functionalization/modifications, as well as other functionalization/modifications that would be appreciated by a person having ordinary skill in the art upon reading the instant disclosure, without departing from the scope of the inventive concepts set forth herein.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A click-chemistry compatible structure, comprising:
   a plurality of photo polymerized molecules structurally arranged according to a multi-layer three-dimensional pattern; and
   wherein surfaces of the structure are functionalized with one or more click-chemistry compatible molecules each having one or more click-chemistry compatible functional groups.

2. The structure as recited in claim 1, wherein the click-chemistry compatible functional groups are configured to engage in a copper-catalyzed azide-alkyne cycloaddition (CuAAC) reaction.

3. The structure as recited in claim 1, wherein at least some of the click-chemistry compatible functional groups comprise a terminal azide group.

4. The structure as recited in claim 3, wherein at least some other of the click-chemistry compatible functional groups comprise a terminal alkyne group.

5. The structure as recited in claim 1, wherein the photo polymerized molecules are each independently selected from the group consisting of: crosslinked hexane diol diacrylate (HDDA), crosslinked polyethylene glycol diacrylate (PEGDA), crosslinked pentaerythritol triacrylate (PETA), crosslinked ethylene glycol dimethacrylate (EGDMA) and combinations thereof.

6. The structure as recited in claim 1, wherein at least some of the click-chemistry compatible molecules are functionalized with one or more organic additives selected from a group consisting of:
   an antibiotic;
   an antibacterial compound; and
   silica dioxide nanoparticles.

7. The structure as recited in claim 1, wherein at least some of the click-chemistry compatible functional groups are functionalized to form a self-assembled monolayer (SAM), wherein the SAM comprises either or both of: an azide-terminated poly(polyethylene glycol) methacrylate derivative; and an alkyne-terminated poly(polyethylene glycol) methacrylate derivative.

8. The structure as recited in claim 1, wherein the structure is porous.

9. The structure as recited in claim 1, wherein the structure is characterized by features having a size in a range from about three-hundred nanometers to about one thousand microns.

10. The structure as recited in claim 1, wherein a bulk of the structure comprises the photo polymerized molecules; and
    wherein the surfaces functionalized with the one or more click-chemistry compatible molecules also comprise the photo polymerized molecules.

11. The structure as recited in claim 1, wherein the three-dimensional pattern comprises an octahedral truss.

12. The structure as recited in claim 1, wherein the click-chemistry compatible functional groups are protected from participating in a click-chemistry reaction via one or more protecting groups functionalized to the click-chemistry compatible functional groups; and
    wherein the one or more protecting groups are each independently selected from the group consisting of: a triethylsilyl (TES), a t-butyldimethylsilyl (TBS) group, a triisopropylsilyl (TIPS) group, a 2-(2-hydroxypropyl) group, and combinations thereof.

13. A method of forming the structure as recited in claim 1, the method comprising:
    exposing, according to the three-dimensional pattern, portions of an additive manufacturing resin to a wavelength of light configured to cause a photo polymerizable compound in the additive manufacturing resin to polymerize into a solid layer of the structure; and wherein the additive manufacturing resin comprises at least one compound having a click-chemistry compatible functional group.

14. A method of functionalizing the structure as recited in claim 1, the method comprising:
reacting the structure with an organic additive;
wherein the organic additive comprises one or more click-chemistry compatible functional groups other than the click-chemistry compatible functional groups of the click-chemistry compatible molecules functionalized on the surfaces of the structure;
wherein the click-chemistry compatible molecules functionalized on the surfaces of the structure are structurally configured to react with the one or more click-chemistry compatible functional groups of the organic additive and thereby attach the organic additive to the structure via the click-chemistry compatible molecules functionalized on the surfaces of the structure; and
wherein the click-chemistry compatible functional groups of the click-chemistry compatible molecules functionalized on the surfaces of the structure are each independently selected from a group consisting of: a terminal alkyne and a terminal azide.

15. The method as recited in claim 14, wherein the organic additive is selected from a group consisting of:
an antibiotic;
an antibacterial compound; and
silica dioxide nanoparticles.

16. The method as recited in claim 14, the reacting comprising functionalizing at least some of the click-chemistry compatible functional groups functionalized on the surfaces of the structure to form a self-assembled monolayer (SAM).

17. An additive manufacturing resin suitable for fabricating a click-chemistry compatible structure, the resin comprising a click-chemistry compatible oligomer, wherein the click-chemistry compatible oligomer comprises:

one or more click-chemistry compatible functional groups; and
one or more photo polymerizable moieties; and
wherein the click-chemistry compatible functional groups are protected from participating in a click-chemistry reaction via one or more protecting groups functionalized to the click-chemistry compatible functional groups.

18. The additive manufacturing resin of claim 17, wherein the oligomer is both click-chemistry compatible and exhibits a photo polymerizable capability;
wherein the click-chemistry compatibility of the oligomer and the photo polymerizable capability of the oligomer are respectively conveyed via different functional groups of the oligomer; and
wherein the one or more photo polymerizable moieties each independently comprise a functional group selected from the group consisting of: an acrylate, an epoxide, a thiol-ene, a vinyl ether, and an N-vinyl carbazole.

19. The additive manufacturing resin of claim 18, wherein the one or more photo polymerizable moieties each independently comprise either the vinyl ether or the N-vinyl carbazole.

20. The additive manufacturing resin as recited in claim 17, further comprising: a second click-chemistry compatible oligomer, and a third click-chemistry compatible oligomer;
wherein the click-chemistry compatible oligomer comprises a click-chemistry compatible functional group and an acrylate group;
wherein the second click-chemistry compatible oligomer comprises a second click-chemistry compatible functional group and an epoxide group; and
wherein the third click-chemistry compatible oligomer comprises a third click-chemistry compatible functional group and a thiol-ene group.

* * * * *